(12) United States Patent
Borini et al.

(10) Patent No.: US 10,467,882 B2
(45) Date of Patent: Nov. 5, 2019

(54) APPARATUS FOR DETECTING HUMIDITY

(71) Applicant: Nokia Technologies Oy, Espoo (FI)

(72) Inventors: Stefano Borini, Cambridge (GB); Di Wei, Cambridge (GB)

(73) Assignee: Nokia Technologies Oy, Espoo (FI)

( * ) Notice: Subject to any disclaimer, the term of this patent is extended or adjusted under 35 U.S.C. 154(b) by 0 days.

(21) Appl. No.: 15/547,625

(22) PCT Filed: Jan. 28, 2016

(86) PCT No.: PCT/FI2016/050042
§ 371 (c)(1),
(2) Date: Jul. 31, 2017

(87) PCT Pub. No.: WO2016/124812
PCT Pub. Date: Aug. 11, 2016

(65) Prior Publication Data
US 2018/0025613 A1  Jan. 25, 2018

(30) Foreign Application Priority Data
Feb. 6, 2015  (EP) .................................. 15154046

(51) Int. Cl.
*G08B 21/00* (2006.01)
*G08B 21/20* (2006.01)
*H01M 6/32* (2006.01)
*G01N 33/02* (2006.01)

(52) U.S. Cl.
CPC .............. *G08B 21/20* (2013.01); *H01M 6/32* (2013.01); *G01N 33/02* (2013.01)

(58) Field of Classification Search
CPC .......... G08B 21/20; H01M 6/32; G01N 33/02

USPC ........................................................ 340/602
See application file for complete search history.

(56) References Cited

U.S. PATENT DOCUMENTS

| 4,598,273 A | * | 7/1986 | Bryan, Jr. ............. | E04D 13/006 |
| | | | | 200/61.04 |
| 4,651,121 A | * | 3/1987 | Furubayashi ........ | G01N 27/225 |
| | | | | 338/34 |
| 5,224,373 A | * | 7/1993 | Williams ............. | G01N 31/222 |
| | | | | 73/29.02 |

(Continued)

FOREIGN PATENT DOCUMENTS

WO    03078300    9/2003

OTHER PUBLICATIONS

Hyuu-Woo Yu, Self-Powered Humidity Sensor Based on Graphene Oxide Composite Film Intercalated by Poly(Sodium 4-Styrenesulf0nate), (Year: 2014).*

(Continued)

*Primary Examiner* — Zhen Y Wu
(74) *Attorney, Agent, or Firm* — Harrington & Smith

(57) ABSTRACT

An apparatus comprising: a humidity-dependent electrical energy source configured to provide electrical energy when an environment occupied by the humidity-dependent electrical energy source becomes humid; and an electrically activated visual indicator coupled to receive provided electrical energy from the humidity-dependent electrical energy source and configured to provide a visual indication that the environment occupied by the humidity-dependent electrical energy source has become humid.

13 Claims, 2 Drawing Sheets

(56) References Cited

U.S. PATENT DOCUMENTS

| | | | | |
|---|---|---|---|---|
| 5,515,723 A * | 5/1996 | Tsuchida | | G01N 27/121 73/29.02 |
| 5,796,345 A * | 8/1998 | Leventis | | A61F 13/42 340/604 |
| 5,841,021 A * | 11/1998 | De Castro | | G01N 27/4162 73/23.2 |
| RE45,186 E * | 10/2014 | Shen | | G01N 33/004 204/412 |
| 2008/0149139 A1* | 6/2008 | Lin | | A61L 2/186 134/18 |
| 2009/0139301 A1* | 6/2009 | Gunsay | | G01N 27/223 73/1.73 |
| 2011/0169650 A1* | 7/2011 | Holloway | | F16P 3/14 340/653 |
| 2011/0199219 A1* | 8/2011 | Smith | | A62B 99/00 340/604 |
| 2012/0190292 A1* | 7/2012 | Skrepcinski | | F24F 7/007 454/258 |
| 2014/0196522 A1* | 7/2014 | Borini | | G01N 7/00 73/29.03 |
| 2014/0247529 A1* | 9/2014 | Borini | | H02H 5/083 361/91.2 |
| 2015/0130637 A1* | 5/2015 | Sengstaken, Jr. | | G08C 17/02 340/870.16 |
| 2015/0211989 A1* | 7/2015 | Van Mechelen | | G01N 21/3581 427/10 |
| 2016/0062318 A1* | 3/2016 | Abhishek | | A61J 7/0427 368/10 |
| 2016/0223490 A1* | 8/2016 | Astley | | G01N 27/4071 |
| 2016/0293973 A1* | 10/2016 | Wei | | G01N 27/4141 |
| 2016/0316501 A1* | 10/2016 | Roe | | G06F 13/42 |

OTHER PUBLICATIONS

International Search Report and Written Opinion received for corresponding Patent Cooperation Treaty Application No. PCT/FI2016/050042, dated May 2, 2016, 10 pages.

* cited by examiner

APPARATUS FOR DETECTING HUMIDITY

RELATED APPLICATION

This application was originally filed as PCT Application No. PCT/FI2016/050042 filed Jan. 28, 2016 which claims priority benefit from EP Patent Application No. 15154046.5, filed Feb. 6, 2015.

TECHNOLOGICAL FIELD

Embodiments of the present invention relate to an apparatus and a method. In particular, they relate to detectors that detect when a sealed container has become unsealed.

BACKGROUND

It may be desirable for an apparatus to detect when a sealed container has become unsealed.

BRIEF SUMMARY

According to various, but not necessarily all, embodiments of the invention there is provided an apparatus comprising: a humidity-dependent electrical energy source configured to provide electrical energy when an environment occupied by the humidity-dependent electrical energy source becomes humid; and an electrically activated visual indicator coupled to receive provided electrical energy from the humidity-dependent electrical energy source and configured to provide a visual indication that the environment occupied by the humidity-dependent electrical energy source has become humid.

According to various, but not necessarily all, embodiments of the invention there is provided an apparatus comprising: a sealed container defining an interior space comprising a controlled low-humidity atmosphere; a product within the interior space; a humidity-dependent electrical energy source configured to provide electrical energy when humidity enters the interior space; and an electrically activated visual indicator coupled to receive provided electrical energy from the humidity-dependent electrical energy source and configured to provide a visual indication of humidity entering the interior space.

According to various, but not necessarily all, embodiments of the invention there is provided an apparatus comprising: a sealable container defining an interior space for containing a product within a controlled low-humidity atmosphere; a humidity-dependent electrical energy source configured to provide electrical energy when humidity enters the interior space; and an electrically activated visual indicator coupled to receive provided electrical energy from the humidity-dependent electrical energy source and configured to provide a visual indication of humidity entering the interior space.

BRIEF DESCRIPTION

For a better understanding of various examples that are useful for understanding the brief description, reference will now be made by way of example only to the accompanying drawings in which.

Figure 5:
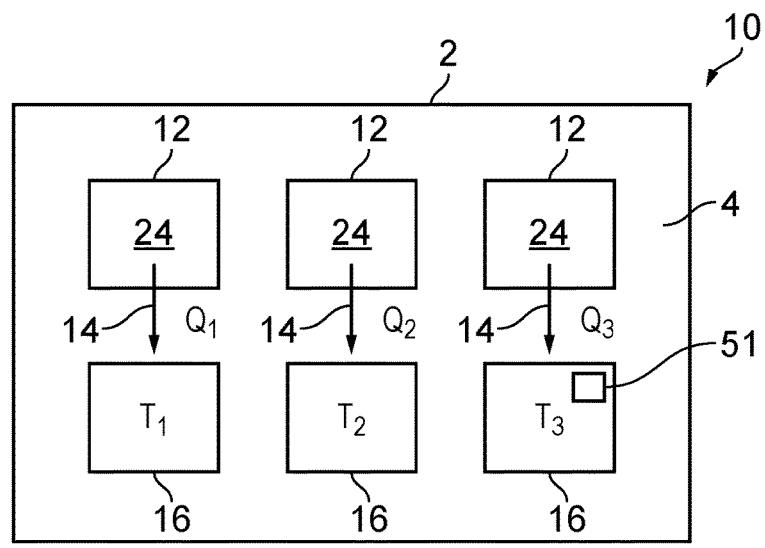
Figures 6A, 6B, 6C:
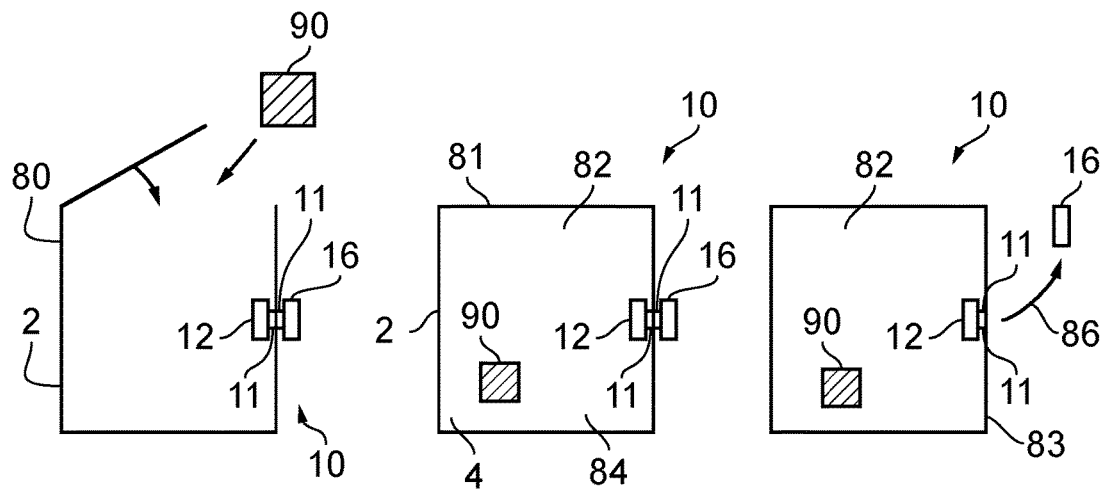

FIG. 5 schematically illustrates an apparatus comprising multiple different proton battery cells each of which is coupled to a different one of multiple electrically activated visual indicators;

FIG. 6A illustrates an example where the container is a sealable container;

FIG. 6B illustrates an example where the container is a sealed container;

FIG. 6C illustrates an example where the visual indicator is removable.

DETAILED DESCRIPTION

Figure 1:
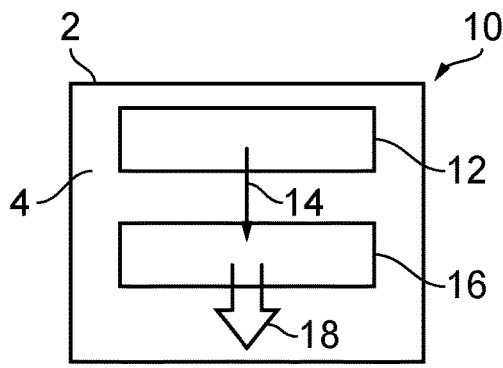
FIGS. 1 and 2 illustrate examples of an apparatus comprising: a humidity-dependent electrical energy source configured to provide electrical energy when an environment occupied by the humidity-dependent electrical energy source becomes humid.
Figure 2:
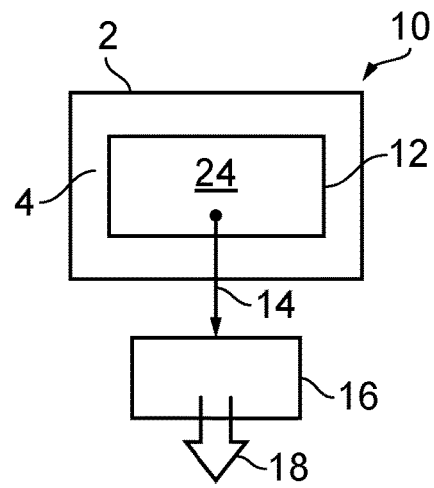

FIGS. 1 and 2 illustrate examples of an apparatus 10 comprising: a humidity-dependent electrical energy source 12 configured to provide electrical energy 14 when an environment 4 occupied by the humidity-dependent electrical energy source 12 becomes humid; and an electrically activated visual indicator 16 coupled to receive provided electrical energy 14 from the humidity-dependent electrical energy source 12 and configured to provide a visual indication 18 that the environment 4 occupied by the humidity-dependent electrical energy source 12 has become humid In FIG. 1, both the humidity-dependent electrical energy source 12 and the electrically activated visual indicator 16 are within a container 2 that defines the environment 4.

In FIG. 2, the humidity-dependent electrical energy source 12 but not the electrically activated visual indicator 16 is within a container 2 that defines the environment 4. The coupling between the electrically activated visual indicator 16 and the humidity-dependent electrical energy source 12 which provides the electrical energy 14 is through the container 2.

It will be appreciated that the apparatus 10 provides a visual indication 18 if the environment 4 becomes humid. This may, for example, occur if the integrity of the container 2 is compromised allowing the ingress of ambient air.

An example of an electrically activated visual indicator 16 is an electro-chromic display. An electro-chromic display is a display that changes its visual appearance in response to an electrical stimulus. The visual appearance may be persistent until another electrical stimulus changes the visual appearance of the display. Examples of electro-chromic displays may, for example, include as active components tungsten trioxide or viologens.

The electrically activated visual indicator 16 may, in response to an electrical stimulus, display a warning sign and/or picture. Where the electrically activated visual indicator 16 comprises electro-chromic material the warning sign and/or picture may be made from the electro-chromic material.

The humidity-dependent electrical energy source 12 may be humidity activated having a de-activated state before exposure to humidity and having an activated state, that provides electrical energy, after exposure to humidity but not before.

Figure 3:
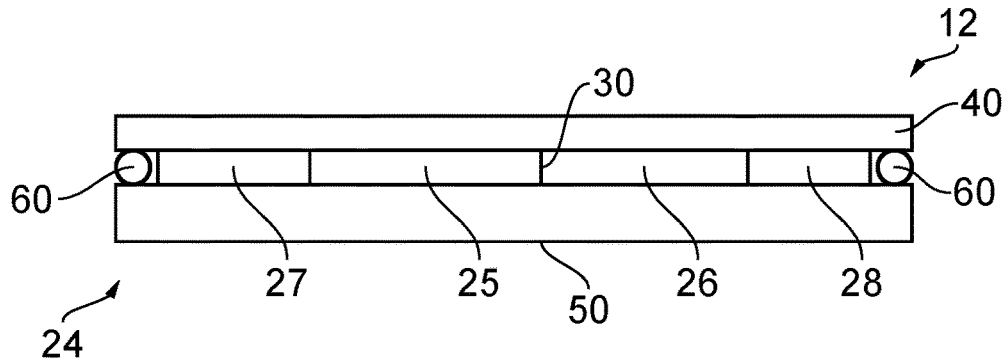
FIG. 3 illustrates an example of a humidity-dependent electrical energy source comprising one or more proton battery cells.

FIG. 3 illustrates an example of a humidity-dependent electrical energy source 12. This humidity-dependent electrical energy source 12 comprises one or more battery cells 24 which in this example are proton battery cells.

Each proton battery cell 24 comprises: a proton conductor region 25 configured to conduct proton charge carriers; an electron conductor region 26 configured to conduct electrons; a first electrode 27 associated with one of the proton conductor region 25; and a second electrode 28 associated with the electron conductor region 26.

In some but not necessarily all examples, the proton conductor region 25 may comprise a graphene derivative and/or comprise graphene oxide and/or comprise charge-donating functional groups comprising one or more of carboxyl, hydroxyl, and epoxy. Such a proton conductor region 25 may be configured to generate and conduct protons in the presence of water.

In some but not necessarily all examples, the electron conductor region 26 may comprise a graphene derivative different to that used in the proton conductor region 25 such as, for example, reduced graphene oxide and/or comprise conjugated polymer.

The first electrodes 27 and second electrodes 28 operate as charge collectors and may be formed from metallic material such as, for example, silver or copper. One or both electrodes may comprise organic materials such as carbon based electrodes or other conductive materials. The first electrodes 27 and/or the second electrodes 28 may be transparent.

In some but not necessarily all examples, the proton conductor region 25 may be formed from printed ink and/or the electron conductor region 26 may be formed from printed ink.

The proton battery cell 24 or, if more than one proton battery cell 24, some or all of the proton battery cells 24 may be two-dimensional, that is the first electrode 27 and the second electrode 28 forming a proton battery cell 24 lie in the same common two-dimensional plane. The proton conductor region 25 and the electron conductor region 26 will also lie in the same two-dimensional plane.

The proton battery cell(s) 24 may be supported by a substrate 50.

The apparatus 12 additionally comprises a buffer layer 40 that is permeable to water vapor overlying the proton battery cell(s) 24.

The buffer layer 40 may be a meshed material. The buffer layer 40 may be hydrophobic and/or non-stick. The buffer layer 40 may be a breathable textile.

In the example illustrated, the buffer layer 40 directly contacts the proton battery cell(s) 24. In the example illustrated, the buffer layer 40 overlies and directly contacts the first electrode 27, the proton conductor region 25, the electron conductor region 26 and the second electrode 28.

In this example, but not necessarily all examples, the buffer layer 40 is adhered to the substrate 50 using a circumscribing perimeter of adhesive 60. The adhesive 60 surrounds, in two-dimensions, the proton battery cell(s) 24.

In this example, but not necessarily all examples, the buffer layer 40 contacts but is not adhered to the proton battery cell(s) 24.

The buffer layer 40 may be flexible. This allows it to adapt to the shape of the proton battery cell(s) 24.

In addition, the substrate 50, the proton battery cell(s) 24 and the buffer layer 40 may be flexible. This allows the whole apparatus 12 to be flexible.

In some but not necessarily all examples, a porous polymer electrolyte may be impregnated into the buffer layer 40.

In some but not necessarily all example, different hydrophilic polymers, such as for example polyvinyl alcohol, may be applied to the buffer layer 40.

The buffer layer 40 may prevent release of particles from the proton battery cell 24.

Figure 4A:
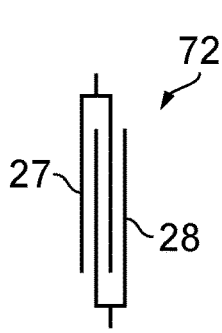
FIGS. 4A, 4B and 4C illustrate examples of an apparatus that has interdigitated proton battery cell electrodes.
Figure 4B:
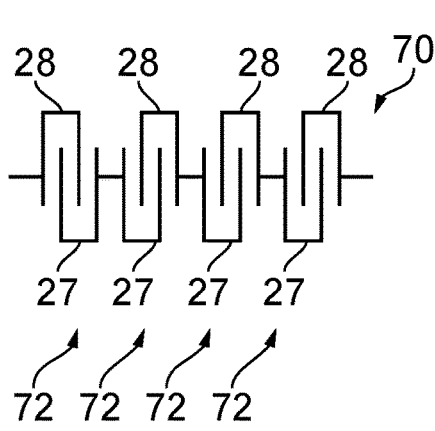

FIGS. 4A and 4B illustrate examples of an apparatus 12 that has interdigitated first electrodes 27 and second electrodes 28. The apparatus 12 is as previously described.

In FIG. 4A, the illustrated apparatus, the humidity-dependent electrical energy source 12, comprises a meandering proton battery cell 72. The meandering proton battery cell 72 operates in a manner similar to three proton battery cells 24, connected in physical and electrical parallel. The meandering proton battery cell 72 is formed using a single U shaped first electrode 27 and a single U shaped second electrode 28, where the U shaped first electrode 27 and the U shaped second electrode 28 are interdigitated. In this case, a proton conductor-electron conductor junction between the proton conductor region 25 and the electron conductor region 26 would follow the interdigitated gap between the first electrode 27 and the second electrode 28. Interdigitation increases the length of the proton conductor-electron conductor junction.

Figure 4C:
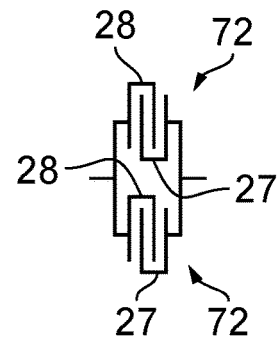

In FIGS. 4B and 4C, the illustrated apparatus 12 comprises a plurality 70 of proton battery cells 24 each of which has a first electrode 27 and a second electrode 28. In the illustrated example, the apparatus 12 comprises multiple meandering proton battery cells 72. Each meandering proton battery cell 72 operates in a manner similar to three battery cells 24, connected in physical and electrical parallel. The meandering proton battery cell 72 is formed using a single U shaped first electrode 27 and a single U shaped second electrode 28, where the U shaped first electrode 27 and the U shaped second electrode 28 are interdigitated as illustrated.

In FIG. 4B, each of four meandering proton battery cells 72 is connected in electrical series to the next meandering proton battery cell 72 in the series of four meandering proton battery cells 72.

In FIG. 4C, each of two meandering proton battery cells 72 is connected in electrical parallel to the adjacent meandering proton battery cell 72 in the series of four meandering proton battery cells 72.

It will be appreciated that each proton battery cell 24 (or meandering proton battery cell 72) is a battery unit and the battery units may be connected in series to achieve a controlled voltage as illustrated in FIG. 4B, or connected in parallel to achieve a controlled electrical current as illustrated in FIG. 4C or connected as a network of battery units in series and/or parallel to achieve both a controlled voltage and a controlled electric current.

FIG. 5 schematically illustrates an apparatus 10 comprising multiple different humidity-dependent electrical energy sources 12. Each humidity-dependent electrical energy source 12 may comprise one or more proton battery cells 24, which may or may not include meandering proton battery cells 72. Each humidity-dependent electrical energy source 12 is coupled to a different one of multiple electrically activated visual indicators 16.

According to one implementation, the multiple different humidity-dependent electrical energy sources 12 each produce different electric charge $Q_n$ (electric current) in response to the same levels of humidity within a common shared environment 4 within the container 2. Each one of the multiple electrically activated visual indicators 16 is coupled to receive electrical energy 14 (electric charge $Q_n$) from one of the multiple different humidity-dependent electrical energy sources 12. Each one of multiple electrically activated visual indicators 16 is activated at the same or similar electric charge threshold and consequently provides a visual indication 18 that the environment 4 occupied by the humidity-dependent electrical energy source 12 has become humid after different exposure times. Activation of a visual indication 18 may comprise switching the electrically activated visual indicators 16 from a first non-alert state to a second alert state. In some but not necessarily all examples, the second alert state may be a persistent state that is maintained in the absence of electrical energy 14 from the associated humidity-dependent electrical energy source 12.

In the second alert state, the electrically activated visual indicators 16 may display a warning sign and/or picture made from electro-chromic material.

According to another implementation, the multiple different humidity-dependent electrical energy sources 12 each produce the same or similar electric charge $Q_n$ (electric current) in response to the same levels of humidity within a common shared environment 4 within the container 2. Each one of multiple electrically activated visual indicators 16 is coupled to receive electrical energy 14 (electric charge $Q_n$) from one of the multiple different humidity-dependent electrical energy sources 12. Each one of the multiple electrically activated visual indicators 16 is activated at a different electric charge threshold $T_n$ and consequently provides a visual indication 18 that the environment 4 occupied by the humidity-dependent electrical energy source 12 has become humid after different exposure times. Activation of a visual indication 18 may comprise switching the electrically activated visual indicators 16 from a first non-alert state to a second alert state. In some but not necessarily all examples, the second alert state may be a persistent state that is maintained in the absence of electrical energy 14 from the associated proton battery cell 24.

Proton battery cells 24 may be engineered to produce different electric charge $Q_n$ (electric current) in response to the same levels of humidity by using different lengths of interfaces between the proton conductor region 25 and the electron conductor region 26 or by using other electrical parallel arrangements.

One or more of the electrically activated visual indicators 16 in the second alert state may use a clock 51 to provide a time dependent output as the visual indication 18.

FIG. 6A illustrates an example of the apparatus 10, where the container 2 is a sealable container 80.

The sealable container 80, when sealed (as illustrated in FIG. 6B) defines an interior space 82, comprising a controlled low-humidity atmosphere 84, as the environment 4.

One or more humidity-dependent electrical energy sources 12 are configured to provide electrical energy 14 when humidity enters the interior space 82 and the one or more electrically activated visual indicators 16 are configured to provide one or more visual indications 18 of humidity entering the interior space 82. The one or more humidity-dependent electrical energy sources 12 are located within sealable container 80 in what will be the interior space 82 of the sealed container.

The apparatus 10 of FIG. 6A therefore comprises: a sealable container 80 defining an interior space 82 for containing a product 90 within a controlled low-humidity atmosphere 84; a humidity-dependent electrical energy source 12 configured to provide electrical energy 14 when humidity enters the interior space 82; and an electrically activated visual indicator 16 coupled to receive provided electrical energy 14 from the humidity-dependent electrical energy source 12 and configured to provide a visual indication 18 of humidity entering the interior space 82.

The one or more the electrically activated visual indicators 16 are coupled to receive the provided electrical energy 14 from the one or more humidity-dependent electrical energy sources 12 via conductive interconnects 11 through the container 80.

As illustrated in FIG. 6A, the product 90 is placed within the sealable container 80. A dry atmosphere is created within the sealable container 80 and the sealable container 80 is then sealed to create a sealed container 81 that seals with an interior space 82 the product 90 and a controlled low-humidity atmosphere 84. The atmosphere 84 within the sealed container 81 is low humidity in that it has a lower humidity than the ambient atmosphere outside the sealed container 81. The sealed container 81 is preferable hermetically sealed.

The low-humidity atmosphere 84 may be a low-pressure (vacuum) atmosphere.

The product 90 may be a product that changes in a humid atmosphere. For example, it may be a food product that spoils in a humid atmosphere or when exposed to an ambient atmosphere. The product 90 may be a perishable food and the sealed container 81 may be food packaging.

FIG. 6B illustrates the apparatus 10 comprising: a sealed container 81 defining an interior space 82 comprising a controlled low-humidity atmosphere 84; a product 90 within the interior space 82; a humidity-dependent electrical energy source 12 configured to provide electrical energy 14 when humidity enters the interior space 82; and an electrically activated visual indicator 16 coupled to receive provided electrical energy 14 from the humidity-dependent electrical energy source 12 and configured to provide a visual indication 18 of humidity entering the interior space 82.

As illustrated in FIG. 6C, the one or more the electrically activated visual indicators 16 may be physically removed (detached) 86 from an exterior 83 of the container 2. The removed one or more of the electrically activated visual indicators 16 may, for example, be disposable and/or re-usable.

The term 'comprise' is used in this document with an inclusive not an exclusive meaning. That is any reference to X comprising Y indicates that X may comprise only one Y or may comprise more than one Y. If it is intended to use 'comprise' with an exclusive meaning then it will be made clear in the context by referring to "comprising only one . . . " or by using "consisting".

In this brief description, reference has been made to various examples. The description of features or functions in relation to an example indicates that those features or functions are present in that example. The use of the term 'example' or 'for example' or 'may' in the text denotes, whether explicitly stated or not, that such features or functions are present in at least the described example, whether described as an example or not, and that they can be, but are not necessarily, present in some of or all other examples. Thus 'example', 'for example' or 'may' refers to a particular instance in a class of examples. A property of the instance can be a property of only that instance or a property of the class or a property of a sub-class of the class that includes some but not all of the instances in the class. It is therefore implicitly disclosed that a features described with reference to one example but not with reference to another example, can where possible be used in that other example but does not necessarily have to be used in that other example.

Although embodiments of the present invention have been described in the preceding paragraphs with reference to various examples, it should be appreciated that modifications to the examples given can be made without departing from the scope of the invention as claimed.

Features described in the preceding description may be used in combinations other than the combinations explicitly described.

Although functions have been described with reference to certain features, those functions may be performable by other features whether described or not.

Although features have been described with reference to certain embodiments, those features may also be present in other embodiments whether described or not.

Whilst endeavoring in the foregoing specification to draw attention to those features of the invention believed to be of particular importance it should be understood that the Applicant claims protection in respect of any patentable feature or combination of features hereinbefore referred to and/or shown in the drawings whether or not particular emphasis has been placed thereon.

We claim:

1. An apparatus comprising:
one or more humidity-dependent electrical energy sources configured to provide electrical energy when air of an environment occupied by the one or more humidity-dependent electrical energy sources becomes humid;
one or more electrically activated visual indicators coupled to receive provided electrical energy from the one or more humidity dependent electrical energy sources and configured to provide a visual indication that the air of the environment occupied by the one or more humidity-dependent electrical energy sources has become humid; and
wherein the one or more electrically activated visual indicators are switched from a first non-alert state to a second alert state using an electro-chromic display when the one or more electrically activated visual indicators have received different thresholds of electric charge from respective of the one or more humidity-dependent electrical energy sources; and
wherein the one or more humidity-dependent electrical energy sources each produce different electric charges in response to the same levels of humidity by using different lengths of interfaces between a proton conductor region and an electron conductor region.

2. The apparatus as claimed in claim 1, wherein the one or more humidity-dependent electrical energy sources is humidity activated having a de-activated state before exposure to humidity and having an activated state that provides electrical energy after exposure to humidity.

3. The apparatus as claimed in claim 1, comprising:
one or more battery cells, each cell comprising:
the proton conductor region configured to conduct proton charge carriers in the presence of water;
the electron conductor region configured to conduct electrons;
a first electrode associated with one of the proton conductor region and the electron conductor region; and
a second electrode associated with the other of the proton conductor region and the electron conductor region.

4. The apparatus as claimed in claim 3, comprising a buffer layer overlying at least the proton conductor region and the electron conductor region.

5. The apparatus as claimed in claim 4, wherein the buffer layer is meshed material and/or wherein the buffer layer is hydrophobic and/or wherein the buffer layer is breathable textile.

6. The apparatus as claimed in claim 4, wherein the one or more battery cells further comprise multiple different battery cells, each different cell comprising an interface region between the proton conductor region and the electron conductor region, wherein the multiple different battery cells produce different electric currents in response to the same levels of humidity; and
wherein the one or more electrically activated visual indicators comprises multiple electrically activated visual indicators, wherein each of the multiple electrically activated visual indicators is coupled to receive electric charge from one of the multiple different humidity-dependent electrical energy sources and each of the multiple electrically activated visual indicators consequently provides a visual indication that the air of the environment occupied by the one or more humidity-dependent electrical energy sources has become humid after different exposure times.

7. The apparatus as claimed in claim 6, wherein the interface regions of the multiple different battery cells have different lengths.

8. The apparatus as claimed in claim 4, wherein the one or more battery cells are two dimensional and/or wherein the first electrodes and the second electrodes are interdigitated and/or wherein the proton conductor region comprises a graphene derivative, comprises graphene oxide, or comprises charge-donating functional groups comprising one or more of carboxyl, hydroxyl, and epoxy and/or wherein the electron conductor region comprises at least one of: a graphene derivative different to the proton conductor region, reduced graphene oxide and conjugated polymer.

9. The apparatus as claimed in claim 1, wherein at least one of the one or more electrically activated visual indicators in the second alert state uses a clock to provide a time dependent output.

10. The apparatus as claimed in claim 1,
comprising a sealed container defining an interior space, comprising a controlled low-humidity atmosphere, as the environment, the interior space housing one or more products; or comprising a sealable container for defining an interior space, comprising a controlled low-humidity atmosphere, as the environment,
wherein the one or more humidity-dependent electrical energy sources are configured to provide electrical energy when humidity enters the interior space and the one or more electrically activated visual indicators are configured to provide one or more visual indications of humidity entering the interior space.

11. The apparatus as claimed in claim 10, wherein the one or more humidity-dependent electrical energy sources are located within the interior space.

12. The apparatus as claimed in claim 11, wherein one or more of the electrically activated visual indicators are coupled to receive provided electrical energy from the one or more humidity-dependent electrical energy sources via conductive interconnects through the container.

13. The apparatus as claimed in claim 11, wherein one or more of the electrically activated visual indicators are removably detachable from an exterior of the container.

* * * * *